(12) United States Patent
Miyazaki et al.

(10) Patent No.: US 8,515,526 B2
(45) Date of Patent: Aug. 20, 2013

(54) MAGNETIC RESONANCE IMAGING APPARATUS AND MAGNETIC RESONANCE IMAGING METHOD

(75) Inventors: Mitsue Miyazaki, Mount Prospect, IL (US); Satoshi Sugiura, Otawara (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 510 days.

(21) Appl. No.: 12/694,610

(22) Filed: Jan. 27, 2010

(65) Prior Publication Data
US 2010/0198053 A1 Aug. 5, 2010

(30) Foreign Application Priority Data

Feb. 5, 2009 (JP) .................................. 2009-025079
Nov. 11, 2009 (JP) .................................. 2009-258128

(51) Int. Cl.
*A61B 5/055* (2006.01)

(52) U.S. Cl.
USPC .......................................... 600/419; 600/410

(58) Field of Classification Search
USPC .................. 600/410, 419; 324/306, 307, 309
See application file for complete search history.

(56) References Cited

U.S. PATENT DOCUMENTS

| 5,771,893 | A | * | 6/1998 | Kassai et al. | ................... | 600/419 |
| 6,976,013 | B1 | * | 12/2005 | Mah | ................................ | 706/27 |
| 2009/0005670 | A1 | | 1/2009 | Ichinose et al. | | |
| 2009/0309592 | A1 | * | 12/2009 | Furudate | ........................ | 324/306 |

* cited by examiner

*Primary Examiner* — Ruth S Smith
(74) *Attorney, Agent, or Firm* — Nixon & Vanderhye PC

(57) ABSTRACT

A magnetic resonance imaging apparatus includes a first blood flow image acquisition unit and a second blood flow image acquisition unit. The first blood flow image acquisition unit acquires a first blood flow image of a breast of an object without contrast medium. The second blood flow image acquisition unit acquires a second blood flow image without contrast medium with applying a spin labeling pulse by which a region to be tagged is set based on the first blood flow image as a reference image so as to distinguish blood flowing into a desired region.

18 Claims, 8 Drawing Sheets

MAGNETIC RESONANCE IMAGING APPARATUS AND MAGNETIC RESONANCE IMAGING METHOD

BACKGROUND OF THE INVENTION

1. Field of the Invention

The present invention relates to a MRI (magnetic resonance imaging) apparatus and a magnetic resonance imaging method which excite nuclear spin of an object magnetically with a RF (radio frequency) signal having the Larmor frequency and reconstruct an image based on NMR (nuclear magnetic resonance) signals generated due to the excitation, and more particularly, to a magnetic resonance imaging apparatus and a magnetic resonance imaging method which make it possible to perform non-contrast enhanced MRA (Magnetic Resonance Angiography) to obtain a blood flow image without contrast medium.

2. Description of the Related Art

Magnetic Resonance Imaging is an imaging method which excites nuclear spin of an object set in a static magnetic field with a RF signal having the Larmor frequency magnetically and reconstruct an image based on NMR signals generated due to the excitation.

In the field of the magnetic resonance imaging, as a method of obtaining an image of a blood flow, MRA is known. An MRI that uses a contrast medium is referred to as a contrast MRA. By the dynamic contrast enhanced MRA, an breast imaging and differentiation of a tumor depicted in a breast have been conventionally performed (see, for example, Kuhl, CK, Radiology 1999; 211:101-110 and Kuhl, CK Radiology: Volume 244: Number 2-August 2007).

Specifically, time series DCE (dynamic contrast enhanced) images of a breast are acquired by a dynamic imaging of an object into which a contrast medium is injected in advance, and a perfusion curve which indicates the contrast-enhanced effect by the contrast medium, i.e., a temporal variation in the degree of dyeing the breast by the contrast medium, is generated from the DCE images. Then, an examination on whether a tumor imaged in the breast is benign or malignant is performed by examining time variations of a wash-in part and a wash-out part of the contrast medium in the perfusion curve.

However, a blood flow image can not be acquired with a sufficient contrast without acquiring the first point dyed by a contrast medium as a contrast-enhanced effect within 60 seconds after injection of a contrast medium under the conventional method for differentiating a tumor in a breast based on DCE images since the first time phase in which a blood flow image can be acquired with a sufficient contrast is in a wash-in part within about 60 seconds after injection of contrast medium. Consequently, a time resolution is restricted. Further, a spatial resolution is reduced even by a high speed imaging due to the restriction in a time resolution. As a result, imaging a tumor of under 5 mm is difficult in the conventional technique.

Moreover, though the conventional examination of a tumor based on DCE images requires injection of a Gd type of contrast medium, it has recently been pointed out that there is an association between a Gd type of contrast medium and the NSF (Nephrogenic Systemic Fibrosis).

SUMMARY OF THE INVENTION

The present invention has been made in light of the conventional situations, and it is an object of the present invention to provide a magnetic resonance imaging apparatus and a magnetic resonance imaging method which make it possible to acquire blood flow information more easily and safely for differentiating whether a tumor in an object is benign or malignant without restrictions in time resolution and spatial resolution.

Further, it is another object of the present invention to provide a magnetic resonance imaging apparatus and a magnetic resonance imaging method which make it possible to depict even a minute tumor in a breast of an object more satisfactorily and safely without restriction in time resolution.

The present invention provides a magnetic resonance imaging apparatus comprising: a first blood flow image acquisition unit configured to acquire a first blood flow image of a breast of an object without contrast medium; and A second blood flow image acquisition unit configured to acquire a second blood flow image without contrast medium with applying a spin labeling pulse by which a region to be tagged is set based on the first blood flow image as a reference image so as to distinguish blood flowing into a desired region, in an aspect to achieve the object.

The present invention also provides a magnetic resonance imaging apparatus comprising: a first blood flow image acquisition unit configured to acquire a first blood flow image of an object without contrast medium; and a second blood flow image acquisition unit configured to acquire plural second blood flow images without contrast medium with applying spin labeling pulses by which a region to be tagged is set based on the first blood flow image as a reference image so as to distinguish blood flowing into a desired region, the spin labeling pulses having mutually different inversion times, in an aspect to achieve the object.

The present invention also provides a magnetic resonance imaging apparatus comprising: a blood flow image acquisition unit configured to acquire plural blood flow images without contrast medium with applying spin labeling pulses for tagging blood flowing into a desired region of an object so as to be distinguished, a marker including a matter generating a magnetic resonance signal being arranged in the object, the spin labeling pulses having mutually different inversion times; and a normalization unit configured to normalize the blood flow images using a signal value of a magnetic resonance signal from the marker, in an aspect to achieve the object.

The present invention also provides a magnetic resonance imaging method comprising: acquiring a first blood flow image of a breast of an object without contrast medium; and acquiring a second blood flow image without contrast medium with applying a spin labeling pulse by which a region to be tagged is set based on the first blood flow image as a reference image so as to distinguish blood flowing into a desired region, in an aspect to achieve the object.

The present invention also provides a magnetic resonance imaging method comprising: acquiring a first blood flow image of an object without contrast medium; and acquiring plural second blood flow images without contrast medium with applying spin labeling pulses by which a region to be tagged is set based on the first blood flow image as a reference image so as to distinguish blood flowing into a desired region, the spin labeling pulses having mutually different inversion times, in an aspect to achieve the object.

The present invention also provides a magnetic resonance imaging method comprising: acquiring plural blood flow images without contrast medium with applying spin labeling pulses for tagging blood flowing into a desired region of an object so as to be distinguished, a marker including a matter generating a magnetic resonance signal being arranged in the object, the spin labeling pulses having mutually different inversion times; and normalizing the blood flow images using a signal value of a magnetic resonance signal from the marker, in an aspect to achieve the object.

The magnetic resonance imaging apparatus and the magnetic resonance imaging method according to the present invention as described above make it possible to acquire blood flow information more easily and safely for differentiating whether a tumor in an object is benign or malignant without restrictions in time resolution and spatial resolution.

The magnetic resonance imaging apparatus and the magnetic resonance imaging method according to the present invention as described above also make it possible to depict even a minute tumor in a breast of an object more satisfactorily and safely without restriction in time resolution.

DESCRIPTION OF THE PREFERRED EMBODIMENTS

A magnetic resonance imaging apparatus and a magnetic resonance imaging method according to embodiments of the present invention will be described with reference to the accompanying drawings.
(Configuration and Function)

Figure 1:
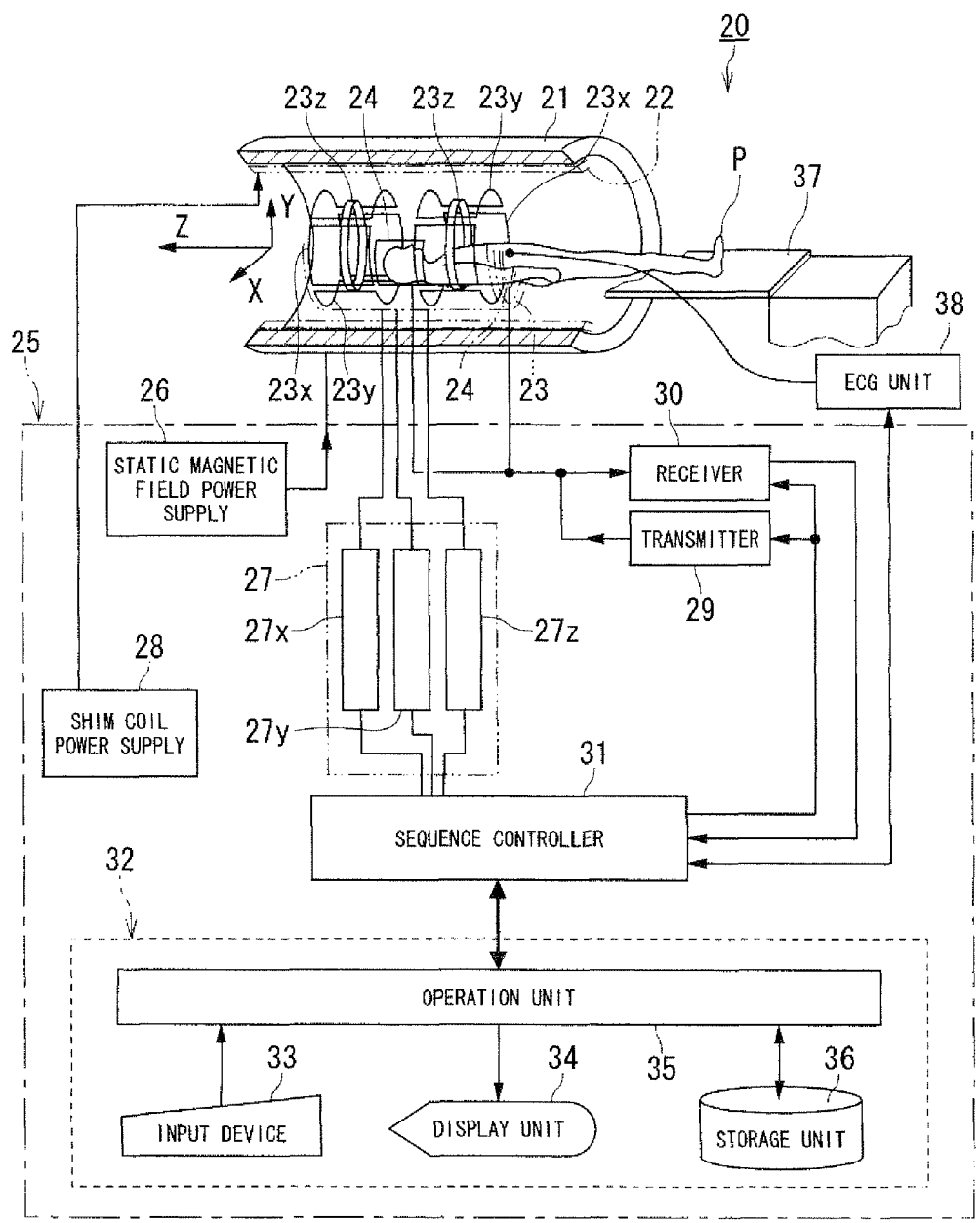
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 has a function to transmit a RF signal given from the transmitter 29 to the object P. The reception RF coil 24 has a function to receive a MR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex data obtained through the detection of a NMR signal and A/D conversion to the NMR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

In addition, an ECG unit 38 for acquiring an ECG (electro cardiogram) signal of the object P is provided with the magnetic resonance imaging apparatus 20. The ECG signal detected by the ECG unit 38 is outputted to the computer 32 through the sequence controller 31.

Note that, a PPG (peripheral pulse gating) signal representing a beat as pulse wave information may be acquired instead of an ECG signal representing a beat as heart rate information. A PPG signal is acquired by detecting a pulse wave of e.g. tip of a finger as an optical signal. When a PPG signal is acquired, a PPG signal detection unit is provided with the magnetic resonance imaging apparatus 20. Hereinafter, a case of acquiring an ECG signal will be described.

The computer 32 gets various functions by the operation unit 35 executing some programs stored in the storage unit 36 of the computer 32. Alternatively, some specific circuits having various functions may be provided with the magnetic resonance imaging apparatus 20 instead of using some of the programs.

Figure 2:
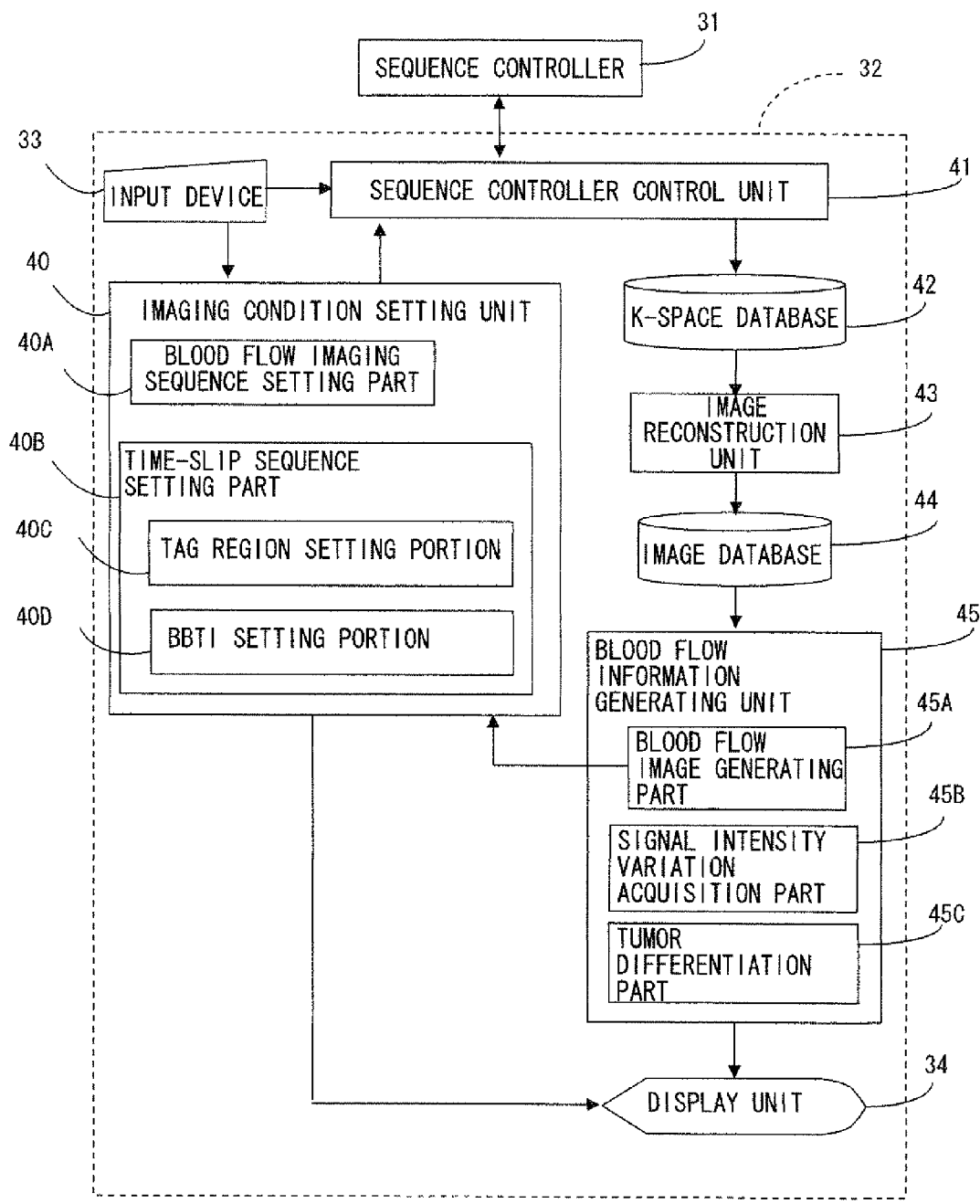
FIG. 2 is a functional block diagram of the computer shown in FIG. 1.

FIG. 2 is a functional block diagram of the computer 32 shown in FIG. 1.

The computer 32 functions as an imaging condition setting unit 40, a sequence controller control unit 41, a k-space database 42, an image reconstruction unit 43, an image database 44 and a blood flow information generating unit 45 by program. The imaging condition setting unit 40 includes a blood flow imaging sequence setting part 40A and a TIME-SLIP (t-SLIP: time-Spatial Labeling Inversion Pulse) sequence setting part 40B which has a tag region setting portion 40C and a BBTI setting portion 40D. The blood flow information generating unit 45 includes a blood flow image generating part 45A, a signal intensity variation acquisition part 45B and a tumor differentiation part 45C.

The imaging condition setting unit 40 has a function to set an imaging condition including a pulse sequence based on information from the input device 33 and to provide the set imaging condition to the sequence controller control unit 42. Especially, the imaging condition setting unit 40 has a function to set a pulse sequence for acquiring a non-contrast enhanced MRA image without using contrast medium under a FBI (flesh blood imaging) method or a SSFP (steady state free precession) method.

As a pulse sequence for the FBI method, a FASE (FastASE: fast asymmetric spin echo or fast advanced spin echo) sequence is known. The EASE sequence is a SE (spin echo) type of sequence for high speed data acquisition using the half-Fourier method. The SSFP sequence using the steady state free precession of nuclear magnetic spins has types of balanced SSFP sequence, true SSFP sequence and the like.

In the FBI method, an ECG-gated imaging is performed using an ECG signal acquired by the ECG unit 38 and echo data is repeatedly acquired per multiple heartbeats after a delay of predetermined time from a trigger signal in synchronization with a reference wave, such as an R wave, representing a cardiac time phase of an object P. Consequently, in the FBI method, the transverse relaxation (T2) component of magnetization of blood recovers by the elapse of the multiple heartbeats, and thus, a water (blood) weighted image in which the T2 magnetization component of the blood is enhanced can be acquired as a blood vessel image. Moreover, in the FBI method, a three dimensional scan for acquiring echo data (volume data) corresponding to a predetermined slice encode amount is performed.

In addition, under the FBI method, an arteriovenous-separated MRA image can be acquired by calculating a subtraction between pieces of image data obtained with mutually different ECG-gated delay times. Specifically, pieces of image data in a systole and a diastole can be acquired in synchronization with an ECG, and subsequently, blood flow image data can be generated by subtraction between the acquired pieces of image data. In this case, differences between arterial signals in the systole and the diastole of the myocardium can be imaged well as an arterial MRA image by applying a spoiler gradient magnetic field pulse to suppress the arterial signals in the systole. In addition, if a dephase pulse or a rephase pulse is applied, relative signal differences between signal values from fast blood flow and slow blood flow can be increased so that arteries and veins can be separated clearly based on the relative signal differences.

Alternatively, an imaging condition for acquiring a non-contrast enhanced MRA image may be set with two dimensional data acquisition or three dimensional data acquisition by a method other than the FBI method. Acquiring non-contrast enhanced MRA image data with three dimensional data acquisition make it possible to generate three dimensional map data representing a characteristic in time variation of signal intensities in blood flow parts as described later.

Moreover, in order to set the foregoing imaging condition, the imaging condition setting unit 40 has a function to display imaging condition setting screen information on the display unit 34. Thus, a user can select an imaging protocol and set an imaging condition such as an excitation region and a region to be tagged (labeled) by operation of the input device 33 with reference to the setting screen displayed on the display unit 34.

The blood flow imaging sequence setting part 40A in the imaging condition setting unit 40 has a function to set a pulse sequence such as a EASE sequence according to the FBI method and a SSFP sequence as described above.

The TIME-SLIP sequence setting part 40B has a function to set a pulse sequence under a TIME-SLIP method by using a blood flow image acquired according to the pulse sequence set by the blood flow imaging sequence setting part 40A as a reference image.

The TIME-SLIP method is a technique for controlling the contrast of an image by applying a spin labeling pulse to label (tag) or distinguish blood flowing into an imaging region as a pre-pulse prior to an imaging sequence such as a FBI sequence or a SSFP sequence. Note that, a spin labeling pulse for spin labeling of blood is called an ASL (Arterial spin labeling) pulse. In the TIME-SLIP method, a TIME-SLIP pulse consisting of multiple ASL pulses is applied.

Figure 3:
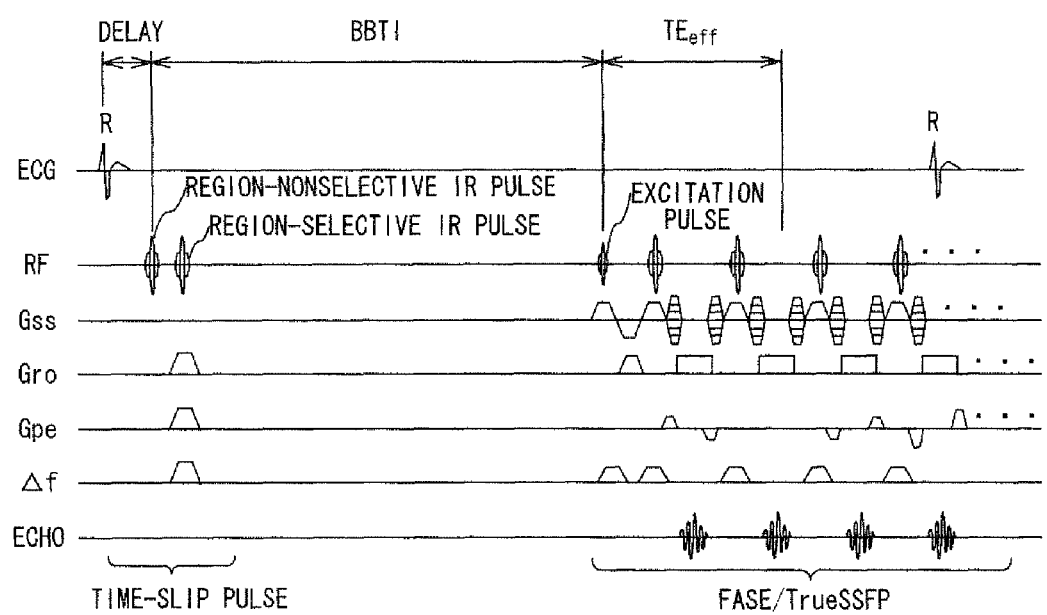
FIG. 3 is a chart showing an example of pulse sequence under a TIME-SLIP method set by the imaging condition setting unit shown in FIG. 2.

FIG. 3 is a chart showing an example of pulse sequence under a TIME-SLIP method set by the imaging condition setting unit 40 shown in FIG. 2.

In FIG. 3, ECG denotes an ECG signal, RF denotes RF transmission pulses, Gss denotes gradient magnetic field pulses for slice selection, Gro denotes gradient magnetic field pulses for RO (readout), Gpe denotes gradient magnetic field pulses for PE (phase encode), Δf denotes gradient magnetic field pulses for adjustment each applied together with an RF transmission pulse and ECHO denotes reception echo signals.

As shown in FIG. 3, in the TIME-SLIP sequence, a TIME-SLIP pulse to label or distinguish blood flowing into an imaging region is applied prior to a EASE sequence under the FBI method or a SSFP sequence such as a TrueSSFP sequence for imaging. That is, the TIME-SLIP sequence is a sequence to selectively image tagged blood flowing into an imaging region, or to suppress blood flow signals so as to distinguish blood flowing from outside into a tagged imaging region.

The TIME-SLIP pulse is applied after the elapse of a certain delay time from an R wave of an ECG signal, and an RF excitation pulse is applied after the elapse of a BBTI (Black Blood Traveling Time) corresponding to an inversion time (TI) from an application timing of the TIME-SLIP pulse. Then, the echo signal at the center of the K-space is acquired after the elapse of an effective TE (echo time) TEeff from application of the RP excitation pulse. Consequently, intensities of signals in only blood having reached an imaging region after the elapse of the BBTI can be enhanced or suppressed.

A TIME-SLIP is configured with a region non-selective IR (inversion recovery) pulse and a region selective IR pulse. A region non-selective IR pulse can be switched into ON/OFF state. Therefore, a TIME-SLIP is configured with only a region selective IR pulse, or alternatively, with both a region selective IR pulse and a region non-selective IR pulse. A region selective IR pulse can be set arbitrarily independent of an imaging region. When a tagging target region set in an imaging region is labeled by a region selective IR pulse with switching the region non-selective IR pulse into the OFF state to invert the longitudinal magnetization, signal intensities in parts to which non-labeled blood (i.e., blood in which longitudinal magnetization does not invert) flowing into the tagged region reaches after a TI become high. Therefore, moving directions and/or moving distances of blood can be recognized. That is, signal intensities corresponding to only blood which reaches to an imaging region after a TI can be enhanced or suppressed selectively.

The TAG region setting portion 40C has a function to use a blood flow image acquired according to the pulse sequence set by the blood flow imaging sequence setting part 40A as a reference image and set a region to be tagged by a TIME-SLIP pulse on the reference image according to the operating information from the input device 33.

The BBTI setting portion 40D has a function to set a BBTI of a TIME-SLIP sequence as an imaging condition for the TIME-SLIP method according to the operating information from the input device 33. It is preferable that the BBTI is set to at least mutually different multiple values.

The sequence controller control unit 41 has a function for controlling the driving of the sequence controller 31 by giving an imaging condition including a pulse sequence, acquired from the imaging condition setting unit 40, to the sequence controller 31 in response to instruction for starting a scan from the input device 33. Further, the sequence controller control unit 41 has a function for receiving raw data from the sequence controller 31 and arranging the raw data to k space formed in the k-space database 42. Therefore, the raw data generated by the receiver 30 is stored as k space data in the k-space database 42.

The image reconstruction unit 43 has a function for reconstructing image data from k-space data by capturing the k-space data from the k-space database 42 and performing image reconstruction processing including FT (Fourier transform) to the k-space data, and writing the generated image data to the image database 44. Therefore, the image database 44 stores the image data reconstructed by the image reconstruction unit 43. Accordingly, image data acquired according to a pulse sequence such as a sequence under the FBI method or a SSFP sequence set by the blood flow imaging sequence setting part 40A and image data corresponding to a single BBTI or mutually different plural BBTIs with application of a TIME-SLIP or TIME-SLIPS set by the TIME-SLIP sequence setting part 40B are stored in the image database 44.

The blood flow information generating unit 4 has a function for performing image processing, required to generate and display blood flow image data, of necessary image data read form the image database 44, generating blood flow information such as blood flow perfusion based on the blood flow image data and displaying the blood flow information and/or the blood flow image data on the display unit 34. The image processing necessary for generating blood flow image data includes subtraction processing between image data corresponding to a diastole and image data corresponding to a systole. The image processing necessary for displaying blood flow image data includes projection processing such as MIP (Maximum Intensity Projection) processing and display processing for displaying a blood flow image identified with respect to each signal intensity such as processing for color-displaying a blood flow image with a color scale corresponding to signal intensities.

The blood flow image generating part 45A has a function to generate blood flow image data using image data acquired from the image database 44 and give spatial position information of blood flow image data generated for setting a region to be tagged by a TIME-SLIP pulse to the tag region setting portion 40C.

The signal intensity variation acquisition part 45B has a function to acquire blood flow image data corresponding to a single BBTI or mutually different plural BBTIs of a TIME-SLIP sequence from the blood flow image generating part 45A and acquire a BBTI value and/or a variation in signal intensity versus a BBTI variation at a specific position as blood flow information. A variation in signal intensity versus a variation in BBTI can be expressed as mathematical values, and alternatively, expressed as a curve by plotting the mathematical values as well. In addition, an index of two dimensional data or three dimensional data representing a characteristic in time variation of signal intensities may be generated.

A variation in signal intensity with respect to a variation in BBTI can be considered as a time variation in signal intensity. Though a curve that shows a variation in signal intensity versus a variation in BBTI is different from the conventional perfusion curve acquired by the dynamic contrast enhanced MRA, the curve can be treated as a perfusion curve since the curve can be regarded as a time variation of blood flow signal. Therefore, a curve showing a variation in signal intensity versus a variation in BBTI is referred as a perfusion curve here. This perfusion curve can be acquired at a single pixel position or every pixel for plural pixel positions in blood flow image data. Therefore, a perfusion curve may be obtained for plural pixel positions included in a desired region such as a region surrounding a tumor part or for all pixel positions.

On the other hand, examples of two dimensional index representing a characteristic of time variation in signal intensity include a gradient, a maximum gradient and/or a time till the maximum gradient of signal intensity variation between mutually different BBTIs at a same pixel position, a signal intensity ratio and/or a signal intensity difference between mutually different BBTIs at a same pixel position, and an average value of signal intensities, a maximum value of signal intensities and/or a time till the maximum value of signal intensities at a same pixel position. Similarly, calculating an index at each voxel position makes it possible to obtain three dimensional data as an index representing a characteristic of time variation in signal intensity.

A method for showing blood flow information, that a two dimensional map or a three dimensional map representing a characteristic of time variation in signal intensity is generated, the two dimensional map or the three dimensional map is displayed, a perfusion curve of a representative value of signal intensity variation is generated for a ROI (region of interest) set on the two dimensional map or the three dimensional map, and the generated perfusion curve is displayed, is a concrete example.

The tumor differentiation part 45C has a function to perform differentiation of whether a malignant tumor exists or whether a tumor part is malignant or benign based on values or time variations of signal intensities in blood flow image data acquired by the signal intensity variation acquisition part 45B to generate a differentiation result as blood flow information.

The time variations in signal intensity of blood flow image data and/or a differentiation result of a tumor generated as the blood flow information in the signal intensity variation acquisition part 45B and the tumor differentiation part 45C can be displayed on the display unit 34. A tumor part can be distinguished with a color and the like. In case where indexes showing characteristics of time variations in signal intensities of blood flow image data are calculated for multiple pixel positions or voxel positions, two dimensional data or three dimensional data of the indexes for the respective positions can be also displayed with identification depending on the degree with a color scale corresponding to values of the indexes showing characteristics of time variations (Operation and Action)

Then, the operation and action of the magnetic resonance imaging apparatus 20 will be described.

Figure 4:
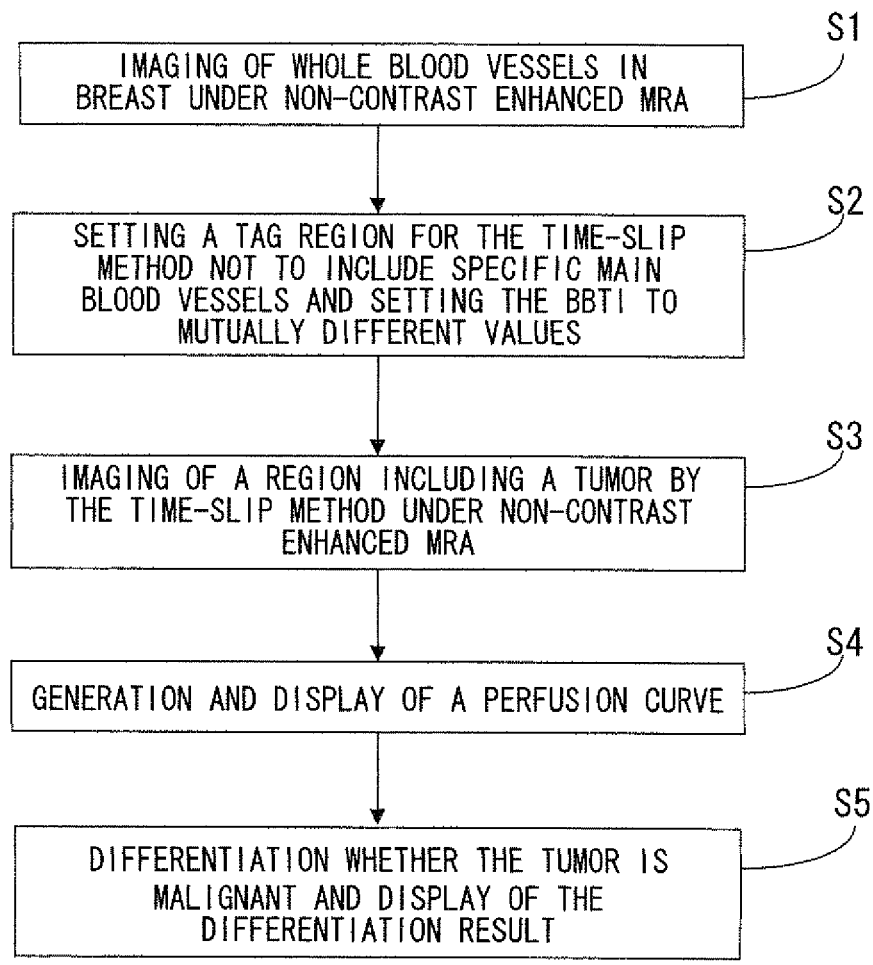
FIG. 4 is a flowchart showing a flow for imaging breast of an object to depict a blood flow image including a tumor, generate blood flow information for differentiating whether the depicted tumor is malignant or not and displaying the blood flow information by the magnetic resonance imaging apparatus shown in FIG. 1.

FIG. 4 is a flowchart showing a flow for imaging breast of an object P to depict a blood flow image including a tumor, generate blood flow information for differentiating whether the depicted tumor is malignant or not and displaying the blood flow information by the magnetic resonance imaging apparatus 20 shown in FIG. 1. The symbols each including S with a number in FIG. 4 indicate respective steps of the flowchart First, in the step S1, blood vessels in the whole breast are imaged under a non-contrast enhanced MRA method. For that purpose, a sequence under the FBI method or a SSFP sequence is set as an imaging condition for an imaging scan in the blood flow imaging sequence setting part 40A in the in the imaging condition setting unit 40. Further, an imaging region is set to a breast part including main blood vessels of an object P. It is preferable that this imaging scan is a scan for acquiring 3D (three dimensional) blood flow image data from the viewpoint of acquiring useful blood flow information with fewer imaging scans. However, an imaging scan for acquiring 2D (two dimensional) blood flow image data may be performed from the viewpoint of shortening of an imaging time.

On the other hand, the object P is set to the bed 37 in advance, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

Then, data acquisition is performed by an imaging scan according to the set imaging condition. Specifically, the input device 33 sends instruction of scan start to the sequence controller control unit 41. The sequence controller control unit 41 supplies the imaging condition including a pulse sequence received from the imaging condition setting unit 40 to the sequence controller 31. Therefore, the sequence controller 31 drives the gradient power supply 27, the transmitter 29, and the receiver 30 in accordance with the pulse sequence received from the sequence controller control unit 41, thereby generating a gradient magnetic field at an imaging area having the set object P, and further generating RF signals from the RF coil 24.

Consequently, the RF coil 24 receives NMR signals generated due to nuclear magnetic resonance in the breast of the object P. Then, the receiver 30 receives the NMR signals from the RF coil 24 and generates raw data which is digital data of NMR signals by A/D conversion subsequently to necessary signal processing. The receiver 30 supplies the generated raw data to the sequence controller 31. The sequence controller 31 supplies the raw data to the sequence controller control unit 41. The sequence controller control unit 41 arranges the raw data as k-space data to the k space formed in the k-space database 42.

Subsequently, the image reconstruction unit 43 reads the k-space data from the k-space database 42 and reconstructs image data. The generated image data is written in the image database 44. Subsequently, the blood flow image generating part 45A of the blood flow information generating unit 45 reads the image data form the image database 44 and performs necessary image processing such as subtraction processing and MIP processing of the image data, thereby generating blood flow image data of the whole breast. The generated blood flow image data of the whole breast is displayed on the display unit 34.

Here, since acquisition of a blood flow image is performed under a non-contrast enhanced MRA method, the blood flow image is unconstrained by a time resolution and a spatial resolution due to conventional contrast medium injection. Consequently, spatial resolutions in a PE direction×a RO direction×a SE (slice encode) direction as an imaging condition can be set to not more than 0.5×0.5×1.0 (0.5 by interpolation) mm, for example. Thus, the above-described data acquisition with a high spatial resolution can depict a tumor having a size of about 3 mm, which has been difficult to be depicted by the contrast-enhanced MRA method, on the blood flow image.

Then in the step S2, an imaging condition including a tag region and a BBTI for a non-contrast enhanced MRA-TIME-SLIP method is set in the TIME-SLIP sequence setting part 40B in the imaging condition setting unit 40 by using the blood flow image displayed on the display unit 34 as a reference image. The pulse sequence is set to a sequence under a FBI method or a SSFP sequence. It is preferable that the pulse sequence should be the sequence used for acquisition of the reference image from the viewpoint of setting an appropriate imaging condition. The imaging scan may be a two dimensional scan or a three dimensional scan.

The BBTI for the TIME-SLIP sequence is set to a single value or multiple values so that the BBTI setting portion 40D can perform differentiation of whether a tumor is malignant or benign. Generally, a tumor is sustained faster from a sustaining blood vessel when the tumor is malignant. Consequently, it is known that the tumor is depicted as a high signal part in both a blood flow image acquired with about BBTI=1000 ms and a blood flow image acquired with about BBTI=2000 ms. Meanwhile, a benign tumor is sustained slower than a malignant tumor. Consequently, it is known that the tumor is not depicted as a high signal part in a blood flow image acquired with about BBTI=1000 ms while the tumor is depicted as a high signal part in a blood flow image acquired with about BBTI=2000 ms.

Therefore, acquiring blood flow image data with setting the BBTI to not more than at least 1300 makes it possible to determine whether a tumor depicted on the blood flow image under the FBI method is malignant or benign. Accordingly, the BBTI is set so as to include at least a value not more than about 1300. Note that, it is preferable to set multiple BBTI values before and after a peak of time variation in signal intensity at a malignant tumor in order to improve the accuracy of tumor differentiation. The BBTI is set to values before and after 1300, such as 700, 1000, 1500, 2000 and 2500.

Meanwhile, a region to be tagged by a TIME-SLIP pulse is set to a region, within the imaging region, which does not include whole or a specific part of main blood vessels toward a breast part possibly becoming feeding arteries to a tumor in the breast part in the tag region setting portion 40C. As a result, non-labeled blood flowing into the tag region within the imaging region from main blood vessels outside the tag region can be selectively depicted. The main blood vessels toward a breast part include perforating branches of the internal mammary artery, the lateral thoracic artery, the thoracodorsal artery, intercostal artery perforators and the thoracoacromial artery.

For example, when a tag region for TIME-SLIP pulse is set so as not to include whole main blood vessels, blood flowing into the tag region from the whole main blood vessels can be selectively depicted. Meanwhile, when a tag region for TIME-SLIP pulse is set so as not to include desired main blood vessels, blood flowing into the tag region from main blood vessels outside of the tag region can be selectively depicted. Consequently, by setting a tag region for TIME-SLIP pulse to a region that does not include target main blood vessels, it is possible to examine and identify which main blood vessel is a feeding artery to a tumor.

Then in the step S3, a region including a tumor is imaged by the non-contrast enhanced MRA-TIME-SLIP method. Specifically, an imaging condition for the non-contrast enhanced MRA-TIME-SLIP method is provided from the imaging condition setting unit 40 to the sequence controller control unit 41, and pieces of blood flow image data corresponding to the BBTIs of the TIME-SLIP method are generated in a procedure similar to that in the imaging of blood vessels in whole breast in the step S1. The generated pieces of blood flow image data are displayed on the display unit 34.

Figure 5:
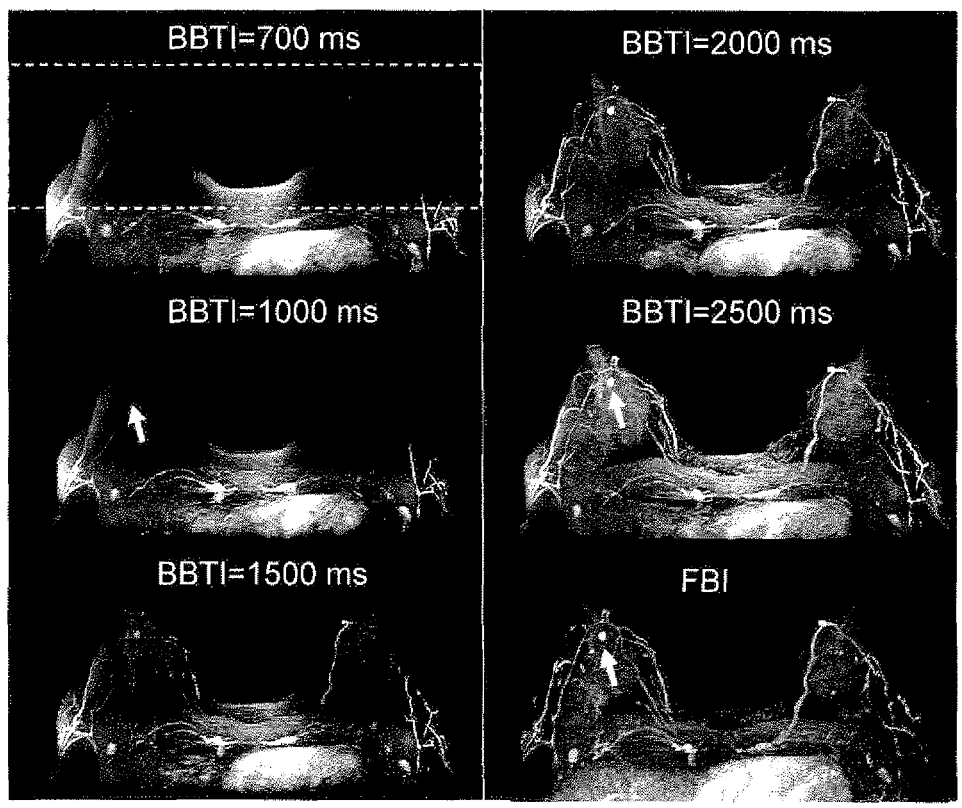
FIG. 5 shows an example of blood flow images of a breast acquired with corresponding to mutually different BBTIs under a TIME-SLIP method and a blood flow image of the breast acquired as a reference image under a FBI method by the magnetic resonance imaging apparatus shown in FIG. 1.

FIG. 5 shows an example of blood flow images of a breast acquired with corresponding to mutually different BBTIs under a TIME-SLIP method and a blood flow image of the breast acquired as a reference image under a FBI method by the magnetic resonance imaging apparatus 20 shown in FIG. 1.

In FIG. 5, blood flow images referred as BBTI=700, 1000, 1500, 2000 and 2500 ms are blood flow images corresponding to the respective BBTIs and blood flow images referred as FBI is a blood flow image of whole blood vessels imaged under the FBI method. The blood flow image of whole blood vessels imaged by the FBI method is used for a reference image to set an imaging condition such as a tag region for TIME-SLIP pulse. In the blood flow image acquired by the FBI method, a tumor can be confirmed at the position indicated by the arrow.

For that reason, as shown by the dotted frame on the blood flow image corresponding to BBTI=700 ms, a region that includes the tumor and that does not include main blood vessels possibly becoming feeding arteries toward the tumor is set as a tag region for TIME-SLIP pulse. Then, blood supplied from main blood vessels to the tag region including the tumor is depicted by the inflow effect of blood according to the BBTI values. Consequently, as shown in FIG. 5, observing blood flow images in the order from a small BBTI value to a large one make it possible to confirm the blood flowing toward the breast.

Meanwhile, it turns out that the tumor confirmed in the reference image acquired by the FBI method can be confirmed as a part showing a medium signal intensity in the blood flow image corresponding to BBTI=2000 ms though the tumor can not be confirmed in the blood flow image corresponding to BBTI=1000 ms. Therefore, it turns out that the variation in signal intensity in the tumor part is small. Accordingly, the tumor depicted in the blood flow image acquired by the FBI method can be differentiated to be benign. In addition, measuring distances between points where blood reached on multiple blood flow images corresponding to mutually different BBTIs allows a velocity of blood flow toward the tumor and a supply time of blood supplied to the tumor to be calculated based on the measured distances and the differences between the BBTIs. Thus, a tumor can also be differentiated based on a blood flow velocity and/or a supply time of blood.

Moreover, a feeding artery to the tumor can be identified by changing a tag region for TIME-SLIP pulse to set the tag region so as not to include only specific main blood vessels as described above and confirming a blood flow image imaged by the non-contrast enhanced TIME-SLIP method visually.

In this way, acquiring a blood flow image of the breast part and the like by a non-contrast enhanced MRA method such as a FBI method allows the blood flow image to have a high spatial resolution since there is no temporal restriction that the blood flow image must be acquired in a wash-in part within the first 60 seconds in which a contrast medium begins to dye as in the case of the conventional contrast enhanced dynamic imaging. This can depict a tumor having a size of about 3 mm, which has been difficult to be depict by the contrast-enhanced MRA method, on the blood flow image. Moreover, by comparing a blood flow image obtained by a non-contrast enhanced MRA method with a blood flow image obtained by a non-contrast enhanced TIME-SLIP method, a user can not only differentiate whether a tumor is benign, but identify a feeding artery to the tumor. This can perform the biopsy with a high accuracy.

Then in the step S4, blood flow information such as a perfusion curve of blood is generated based on pieces of blood flow image data according to the BBTI values in the signal intensity variation acquisition part 45B in the blood flow information generating unit 45. The generated blood flow information is displayed on the display unit 34. For example, in case where only the blood flow image corresponding to a single BBTI value has been acquired, a signal value at a tumor part can be displayed as the blood flow information on the display unit 34.

Alternatively, in case where pieces of blood flow image data corresponding to multiple BBTI values have been acquired, a blood perfusion curve showing a variation in signal value between respective BBTIs at a tumor part and/or map data showing variations in signal values between respective BBTIs at multiple positions can be generated as the blood flow information in the signal intensity variation acquisition part 45B. Since a variation of signal value at a specific position can be regarded as linear, pieces of blood flow image data corresponding to at least mutually different two BBTI values need to be acquired in order to generate a perfusion curve and/or map data.

Moreover, in case of generating a perfusion curve and/or map data, it is preferable to normalize blood flow image data corresponding to each BBTI value by dividing signal intensities of each piece of blood flow image data corresponding to multiple BBTI values by signal intensities of the blood flow image data acquired in the step S1 by the non-contrast enhanced MRA method from the viewpoint of generating useful blood flow information.

In addition, in case of generating a perfusion curve and/or map data, subtracting a reference blood flow image data corresponding to a minimum BBTI value from each of the respective pieces of blood flow image data corresponding to the plural BBTI values can set a signal intensity at a start point of a perfusion curve and/or a minimum value of map data to an appropriate value such as zero and eliminate signal component of background tissues other than blood flow. The above-mentioned subtraction processing may be performed either after or before the normalization. In case of performing the subtraction processing before the normalization, the blood flow image data acquired in the step S1 without tagging under the TIME-SLIP method may be subtracted from each of the respective pieces of blood flow image data corresponding to the plural BBTI values.

Figure 6:
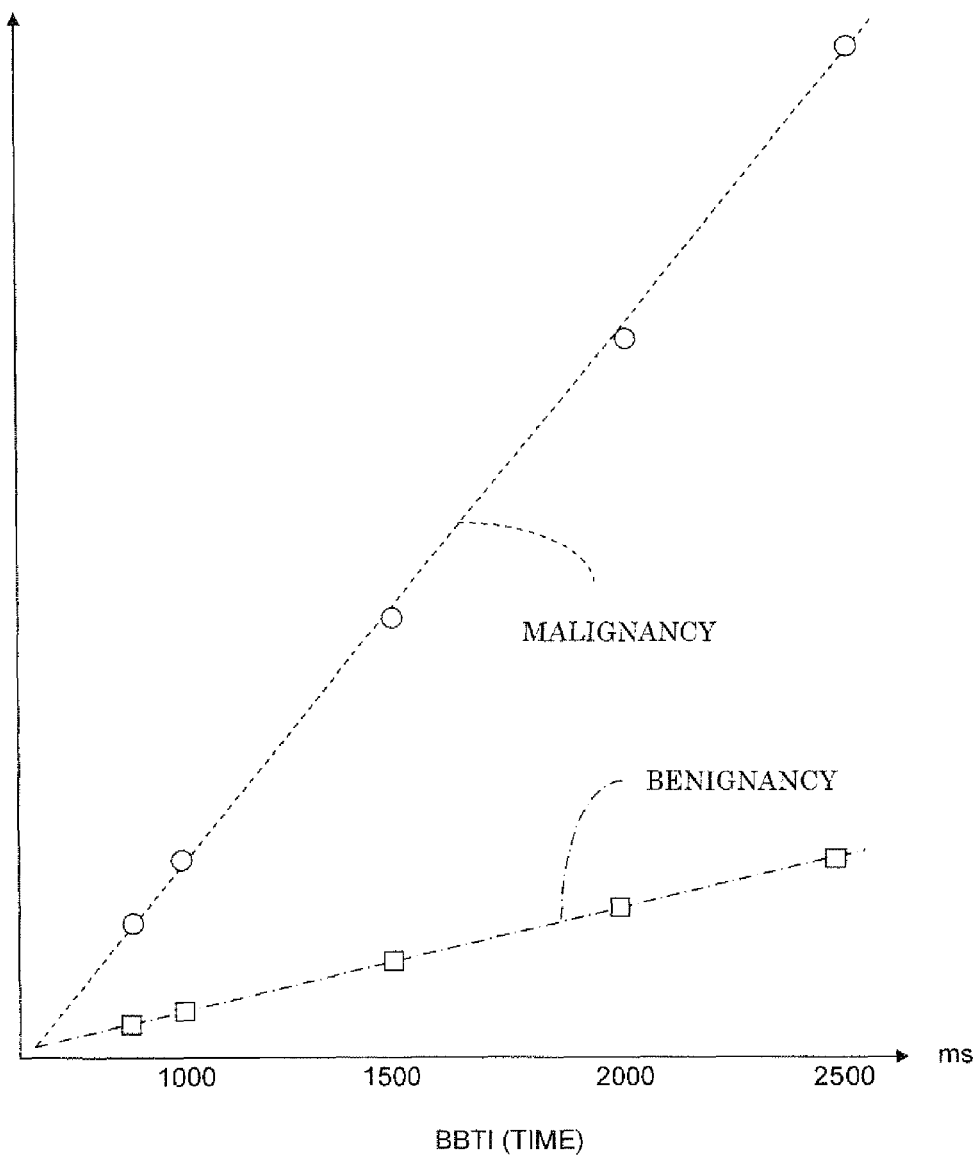
FIG. 6 shows an example of perfusion curve generated by the signal intensity variation acquisition part shown in FIG. 2.

FIG. 6 shows an example of perfusion curve generated by the signal intensity variation acquisition part 45B shown in FIG. 2.

In FIG. 6, the abscissa axis denotes a BBTI, which corresponds to an elapsed time from a reference time, of the TIME-SLIP sequence and the ordinate axis denotes a variation in normalized signal intensity in a tumor part.

As shown in FIG. 6, a non-contrast enhanced perfusion curve showing a time variation in signal intensity of blood at the tumor part can be acquired by plotting the signal intensities at the tumor part on the pieces of blood flow image data corresponding to the multiple BBTI values acquired by the TIME-SLIP method. When the tumor is malignant, the gradient of the perfusion curve becomes large as shown by the circular signs. On the other hand, when the tumor is benign, the gradient of the perfusion curve becomes low as shown by the square signs.

Consequently, when a perfusion curve is displayed, a user can differentiate whether the tumor is malignant or benign more easily by observing the perfusion curve visually.

Meanwhile, the time in the conventional perfusion curve acquired by the contrast enhanced MRA method is affected by an injection velocity of contrast medium, a viscosity of contrast medium and the like. In contrast, the time in a perfusion curve acquired by the non-contrast enhanced MRA-TIME-SLIP method becomes a more accurate perfusion curve which reflects natural blood flow.

In addition, a blood flow perfusion can be observed by time-series subtraction of the signal intensities of the pieces of blood flow image data corresponding to the multiple BBTI values.

When blood flow information such as a perfusion curve and/or map data showing signal intensity variations is acquired, differentiation of a tumor can be performed automatically.

In such a case, in the step S5, differentiation of whether the tumor is malignant is performed by the tumor differentiation part 45C. The differentiation result is displayed on the display unit 34. For example, when blood flow image data corresponding to a single BBTI value has been acquired, the tumor differentiation part 45C can differentiate whether the tumor is malignant or benign by comparing the signal intensity at the tumor part or the signal intensity at the tumor part normalized by the signal intensity of blood flow image data under the non-contrast enhanced MRA method with a preset threshold. When a perfusion curve and/or map data showing signal intensity variations has been acquired based on the pieces of blood flow image data corresponding to a multiple BBTI values, the differentiation of whether the tumor is malignant or benign can be performed by checking the gradient of the curve and/or whether the map data has a singular point.

Consequently, the differentiation of a tumor can be performed without interpretation of a blood flow image by a user. Further, the differentiation of a tumor can be performed uniformly.

That is, the foregoing magnetic resonance imaging apparatus 20 is an apparatus configured to acquire a blood flow image, which can depict a tumor satisfactorily, in a part such as breast by a non-contrast enhanced MRA method such as a FBI method or a SSFP method that can acquire data with a high resolution, and also acquire a blood flow image, which can depict blood supplied to the tumor part, by a non-contrast enhanced TIME-SLIP method. Moreover, the magnetic resonance imaging apparatus 20 is an apparatus configured to generate a perfusion curve of blood flow at a tumor part and/or two or three dimensional map data showing intensity variations in blood flow signals based on pieces of blood flow image data acquired with variable-setting the BBTI value under a non-contrast enhanced TIME-SLIP method so that differentiation of whether the tumor is malignant or benign can be performed based on the generated perfusion curve and/or map data.

(Effect)

According to the foregoing magnetic resonance imaging apparatus 20, a blood flow image can be acquired with a high spatial resolution since data is acquired under a non-contrast enhanced MRA method in which a time resolution is affected by no restriction attributed to an arrival time of contrast medium. Consequently, a small tumor having a size of not more than 5 mm, which is difficult to be depicted under a dynamic contrast enhanced MRA method, can be depicted in a part such as a breast. Moreover, a perfusion curve at a tumor part can be generated based on blood flow image data with a high spatial resolution acquired under a non-contrast enhanced TIME-SLIP method. Consequently, differentiation can be performed for about 3 mm of a small tamer depicted on a blood flow image.

In addition, the TIME-SLIP method can image natural blood flow as an blood flow image since its level of safety is so high because of no contrast medium and also the TIME-SLIP method is unaffected by an injection velocity and a viscosity of contrast medium. Moreover, a perfusion curve reflecting natural blood flow can be generated and differentiation of a tumor can be performed with a higher accuracy.

Further, a feeding artery to a tumor can be specified by adjusting a set position of a region to be tagged by a TIME-SLIP pulse.

MODIFICATIONS

First Modification

The foregoing embodiment describes an example of generating blood flow image data under the flow-in method which images unlabeled blood flowing into a region tagged (labeled) by a TIME-SLIP pulse. However, a region to be tagged including main blood vessels may be set in outside a desired target region including a tumor and blood flow image data can be generated under the flow-out method that labels blood itself to be imaged. In case of the flow-out method, labeled blood flowing into a desired target region is imaged as blood flow image data.

Figure 7:
FIG. 7 shows an example of setting a region to be tagged in case of generating blood flow image data with labeling blood in the magnetic resonance imaging apparatus shown in FIG. 1.

FIG. 7 shows an example of setting a region to be tagged in case of generating blood flow image data with labeling blood in the magnetic resonance imaging apparatus 20 shown in FIG. 1.

As shown in FIG. 7, when a region selective IR pulse is applied with setting a region, including main blood vessels serving as feeding arteries to the breast part, shown by the dotted lines as a region to be tagged, blood supplied into a target region including a tumor shown by the solid lines is labeled. If a region nonselective IR pulse of the TIME-SLIP pulse is set to ON, a longitudinal magnetization in the labeled blood becomes a positive value while a longitudinal magnetization in the background part inverts to a negative value. Consequently, signals from the labeled blood can be acquired selectively as high signal values.

Note that, in case of the flow-out method, subtracting k-space data or image data acquired with application of a region nonselective IR pulse and no region selective IR pulse from k-space data or image data acquired with application of a region nonselective IR pulse and a region selective IR pulse by the different processing make it possible to extract k-space data or image data corresponding to only blood signal component. Thus, blood flow image data in which blood is depicted satisfactorily can be generated by using the extracted data.

Figure 8:
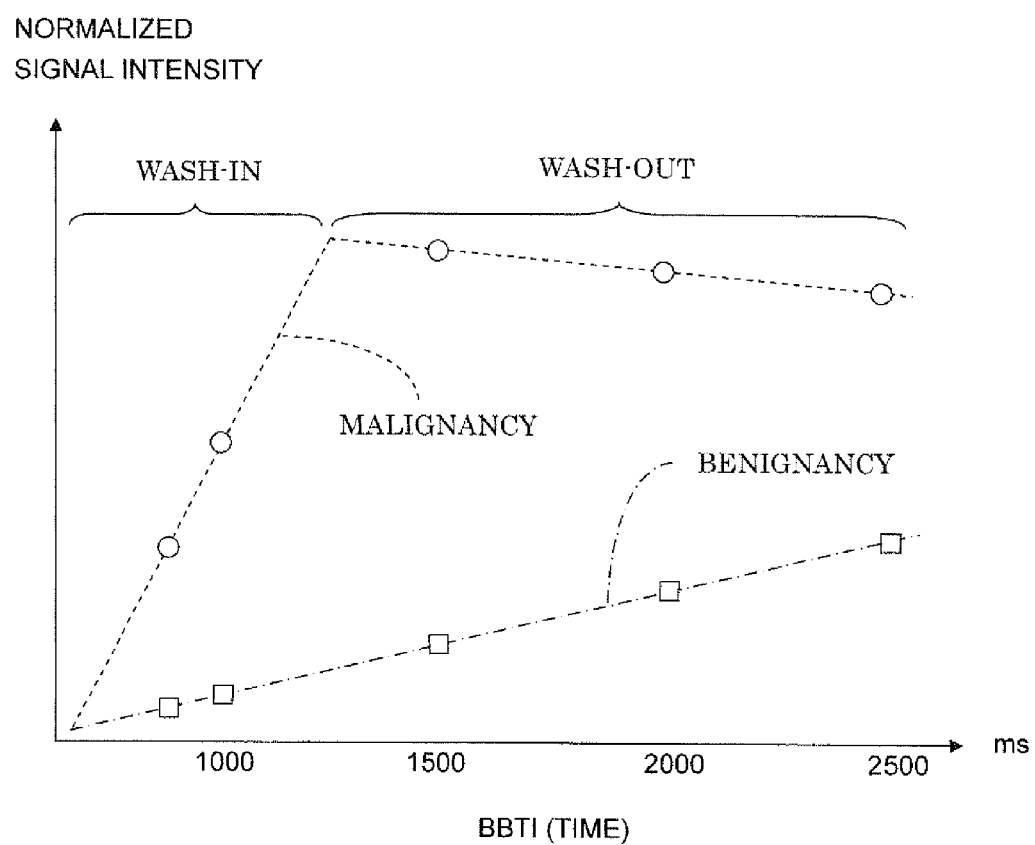
FIG. 8 shows an example of blood perfusion curve generated from blood flow data obtained under a flow-out method with applying a region selective IR pulse to the region to be tagged shown in FIG. 7.

FIG. 8 shows an example of blood perfusion curve generated from blood flow data obtained under a flow-out method with applying a region selective IR pulse to the region to be tagged shown in FIG. 7.

In FIG. 8, the abscissa axis denotes a BBTI, which corresponds to an elapsed time from a reference time, of the TIME-SLIP sequence and the ordinate axis denotes a variation in normalized signal intensity in a tumor part.

When a perfusion curve of blood is generated based on blood flow image data acquired by the flow-out method in the signal intensity variation acquisition part 45B, a curve as shown in FIG. 8 can be acquired. Specifically, in the case of the flow-out method, the obtained perfusion curve shows signal intensity variations in the wash-in part and the wash-out part of blood to and from the tumor part can be acquired.

When the tumor is malignant, the gradient of the perfusion curve in the wash-in part becomes large and the perfusion curve has a peak at the boundary between the wash-in part and the wash-out part as shown by the circular signs. This is because an amount of blood flowing into an imaging region increases over time and subsequently a difference value between the blood signal and the background signal decreases due to recovery of the longitudinal magnetization over further time. Meanwhile, when the tumor is benign, the perfusion curve becomes a rectilinear curve having an approximately constant gradient as shown by the square signs.

Consequently, a user can perform differentiation of whether the tumor is malignant or benign more easily by observing the perfusion curve visually.

Second Modification

The foregoing embodiment and modification describes an example of normalizing multiple pieces of second blood flow image data acquired by a non-contrast enhanced TIME-SLIP FBI method or a non-contrast enhanced TIME-SLIP SSFP method by using the first blood flow image data acquired by a non-contrast enhanced MRA method such as a FBI method or a SSFP method. However, signal values of the multiple pieces of second blood flow image data may be quantified with using only the second blood flow image data acquired by the non-contrast enhanced TIME-SLIP FBI method or the non-contrast enhanced TIME-SLIP SSFP method instead of the first blood flow image data.

For example, a marker containing a matter generating MR signals is placed on the body surface of an object P and multiple pieces of second blood flow image data corresponding to mutually different BBTIs (TIs) are acquired by the TIME-SLIP method. Then, values of MR signals from the marker remains unchanged since the marker is not affected by spin labeling by the TIME-SLIP pulse. Consequently, the signal values of the second blood flow image data can be normalized by using the signal values of the MR signals from the marker.

In this way, when multiple pieces of blood flow image data are normalized by using only the second blood flow image data, the imaging time can be reduced. For example, an imaging by a FBI method is an imaging method that repeats data acquisition for a predetermined slice encode amount per multiple heartbeats. Moreover, an imaging by a TIME-SLIP method requires a time of approximately 2R-R to 3R-R after spin labeling till data acquisition for imaging. Therefore, when the repeating heartbeat is 3R-R, data acquisition for a predetermined slice encode amount in an imaging by a TIME-SLIP method requires approximately 5R-R to 6R-R, i.e., an imaging time becomes relatively long. However, the problem of prolonged imaging time can be resolved since acquisition of the first blood flow image data is not required.

What is claimed is:

1. A magnetic resonance imaging apparatus comprising a computer and associated storage unit configured to:
   set a plurality of inversion times different from each other for differentiating whether a tumor of an object is benign or malignant, each of the plurality of inversion times being an inversion time of a spin labeling pulse for tagging blood in a region to be tagged flowing into an imaging region of the object; and
   acquire a plurality of blood flow images respectively corresponding to the plurality of inversion times, without contrast medium, by applying the spin labeling pulse and an imaging sequence with each of the set plurality of inversion times.

2. A magnetic resonance imaging apparatus as in claim 1, wherein the computer and associated storage unit are further configured to:
   acquire a reference image of the object without contrast medium, the reference image being displayed to assist in setting at least the region to be tagged in acquisition of the plurality of blood flow images.

3. A magnetic resonance imaging apparatus as in claim 2, wherein the computer and associated storage unit are further configured to acquire the plural blood flow images and the reference image of the object without contrast medium by a three dimensional scan for acquiring echo data corresponding to a predetermined slice encode amount every plural beats in synchronization with heart beat information or pulse wave information of the object.

4. A magnetic resonance imaging apparatus as in claim 2, wherein the computer and associated storage unit are further configured to acquire the plural blood flow images and the reference image of the object without contrast medium using a steady state free precession of nuclear magnetic spins.

5. A magnetic resonance imaging apparatus as in claim 2, wherein the computer and associated storage unit are further configured to perform normalization of the plural blood flow images using the reference blood flow image of the object without contrast medium and to generate signal variation information based on the plural blood flow images after the normalization.

6. A magnetic resonance imaging apparatus as in claim 2, wherein the computer and associated storage unit are further configured to acquire the reference image of the object without contrast medium and to differentiate whether a tumor depicted on the reference image is malignant or benign, based on signal intensities of the plural blood flow images.

7. A magnetic resonance imaging apparatus as in claim 2, wherein the computer and associated storage unit are further configured to acquire the reference image of the object without contrast medium and to set the region to be tagged so as to make it possible to specify a blood vessel sustaining a tumor depicted on the reference image.

8. A magnetic resonance imaging apparatus as in claim 2, wherein the computer and associated storage unit are further configured to acquire the reference image of the object without contrast medium and to set the region to be tagged so as to include no main blood vessels depicted on the reference image.

9. A magnetic resonance imaging apparatus as in claim 2, wherein the computer and associated storage unit are further configured to acquire the reference image of the object without contrast medium and to set the region to be tagged so as not to include only a specific main blood vessel depicted on the reference image.

10. A magnetic resonance imaging apparatus as in claim 1, wherein the computer and associated storage unit are further configured to:
   generate signal variation information representing a variation in intensity of a signal from blood versus a variation in inversion time based on the plural blood flow images.

11. A magnetic resonance imaging apparatus as in claim 10, wherein the computer and associated storage unit are further configured to generate the signal variation information as a curve representing variation in signal intensity versus inversion time at a desired position common in the plural blood flow images.

12. A magnetic resonance imaging apparatus as in claim 11, wherein the curve is a perfusion curve showing signal intensity variations in a wash-in part of blood into the tumor.

13. A magnetic resonance imaging apparatus as in claim 11, wherein the curve is a perfusion curve showing signal intensity variations in a wash-in part and a wash-out part of blood into and from the tumor.

14. A magnetic resonance imaging apparatus as in claim 1, wherein the computer and associated storage unit are further configured to set a region involving a main blood vessel as the region to be tagged, the region involving the main blood vessel being outside the imaging region.

15. A magnetic resonance imaging apparatus as in claim 1, wherein the imaging region of the object is a breast.

16. A magnetic resonance imaging apparatus as in claim 1, wherein at least one of the plurality of the inversion times is not more than 1300 ms.

17. A magnetic resonance imaging method comprising:
   setting a plurality of inversion times different from each other for differentiating whether a tumor of an object is benign or malignant, each of the plurality of inversion times being an inversion time of a spin labeling pulse for tagging blood in a region to be tagged flowing into an imaging region of the object; and
   acquiring a plurality of blood flow images respectively corresponding to the plurality of inversion times, without contrast medium, by applying the spin labeling pulse and an imaging sequence with each of the set plurality of inversion times.

18. A magnetic resonance imaging method as in claim 17, further comprising:
   acquiring a reference image of the object without contrast medium, the reference image being displayed to assist in setting at least the region to be tagged in acquisition of the plurality of blood flow images.

* * * * *